(12) United States Patent
Yi

(10) Patent No.: US 7,489,765 B2
(45) Date of Patent: Feb. 10, 2009

(54) COLLIMATOR CONTROL METHOD AND APPARATUS, AND RADIOGRAPHY SYSTEM

(75) Inventor: Fan Yi, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 38 days.

(21) Appl. No.: 11/679,667

(22) Filed: Feb. 27, 2007

(65) Prior Publication Data
US 2007/0206727 A1  Sep. 6, 2007

(30) Foreign Application Priority Data
Mar. 2, 2006  (CN) .................... 2006 1 0058900

(51) Int. Cl.
*G21K 1/02* (2006.01)
(52) U.S. Cl. ........................ 378/151; 378/145
(58) Field of Classification Search ......... 378/147–148, 378/150–153, 37, 64–65; 359/641; 396/449, 396/452, 453, 454, 458
See application file for complete search history.

(56) References Cited

U.S. PATENT DOCUMENTS

| | | | |
|---|---|---|---|
| 4,152,604 A | | 5/1979 | Burbury |
| 5,519,518 A | * | 5/1996 | Watanabe et al. ............. 349/57 |
| 6,215,853 B1 | * | 4/2001 | Kump et al. ................. 378/151 |
| 6,735,360 B2 | | 5/2004 | Mao et al. |
| 6,836,370 B2 | | 12/2004 | Mao et al. |
| 6,931,100 B2 | | 8/2005 | Kato et al. |
| 6,999,556 B2 | | 2/2006 | Nakano |
| 2004/0240621 A1 | * | 12/2004 | Noguchi ..................... 378/150 |
| 2006/0067481 A1 | * | 3/2006 | Morton ....................... 378/151 |

FOREIGN PATENT DOCUMENTS

EP     0193509 B1     9/1986

OTHER PUBLICATIONS

Zou, et al., "Design and Implementation of A DMLC Control System", Proc. Intl. Conf. Comm., Circuits and Systems, May 2005, p. 1181-1185.

* cited by examiner

*Primary Examiner*—Hoon Song
(74) *Attorney, Agent, or Firm*—Armstrong Teasdale LLP

(57) ABSTRACT

The present invention is intended to provide a collimator control method that does not cause blades to get stuck. In a homing phase, blades are positioned based on a blade sense signal sent from a sensor. If the sensor has not sensed the blades but the rotational velocity of a motor has decreased to fall below a predetermined velocity, control states are switched. In a working phase, when an overshoot made by the blades returning to zero positions exceeds a predetermined limit, the control states are switched. Moreover, the rotating direction of the motor is reversed in order to withdraw the blades. Moreover, a collimator is reset to the control state based on tentative zero positions or the control state based on the sense signal sent from the sensor according to whether the sensor has failed.

15 Claims, 7 Drawing Sheets

COLLIMATOR CONTROL METHOD AND APPARATUS, AND RADIOGRAPHY SYSTEM

CROSS REFERENCE TO RELATED APPLICATIONS

This application claims the benefit of Chinese Application No. 200610058900.7 filed Mar. 2, 2006.

BACKGROUND OF THE INVENTION

The present invention relates to a collimator control method and apparatus and a radiography system. More particularly, the present invention is concerned with a method and an apparatus for controlling a collimator that includes motor-driven blades, and a radiography system including the collimator control apparatus.

In radiography systems, a collimator is used to define an X-ray field in a subject to which X-rays are irradiated. The collimator has motor-driven blades. The positions of the blades are varied in order to adjust the X-ray field (refer to, for example, Patent Document 1).

[Patent Document 1] Japanese Unexamined Patent Publication No. 2003-61941 (p. 3 and FIG. 1)

In collimators, blades may be stuck. When it says that the blades are stuck, it means that the blades are immobilized, though a motor is conducting. This is attributable to a malfunction of a driving mechanism or a user's improper manipulation. If the blades are stuck, an X-ray field cannot be adjusted. Consequently, radiography cannot help being interrupted.

SUMMARY OF THE INVENTION

Therefore, an object of the present invention is to realize a collimator control method and apparatus that do not cause blades to get stuck, and a radiography system including the collimator control apparatus.

For solving the aforesaid problem, according to the first aspect of the present invention, there is provided a collimator control method for controlling a collimator that includes motor-driven blades. Herein, an encoder is used to encode rotations made by a motor, a decoder is used to decode a signal sent from the encoder, and a sensor is used to sense whether the blades exist at zero positions. When the collimator enters a homing phase in the first control state, the blades are positioned based on a blade sense signal sent from the sensor. If the sensor has not sensed the blades but the rotational velocity of a motor has decreased to fall below a predetermined speed, the first control state is switched to the second control state.

When the collimator enters a working phase in the first control state, if an overshoot made by the blades returning to the zero positions exceeds a predetermined limit, the first control state is switched to the second control state. When the second control state is designated, the rotating direction of the motor is forcibly reversed in order to withdraw the blades. If an operator performs a manipulation to reset the collimator to the first control state, the collimator is reset to the first control state based on tentative zero positions or the first control state based on the sense signal sent from the sensor.

For solving the aforesaid problem, according to the second aspect of the present invention, there is provided a collimator control apparatus for controlling a collimator that includes motor-driven blades. Herein, the apparatus includes: an encoder that encodes rotations made by a motor; a decoder that decodes a signal sent from the encoder; a sensor that senses whether the blades exist at zero positions; and a control means that when the collimator enters a homing phase in the first control state, positions the blades on the basis of a blade sense signal sent from the sensor, that if the sensor has not sensed the blades but the rotational velocity of a motor has decreased to fall below a predetermined velocity, switches the first control state to the second control state, that when the collimator enters a working phase in the first control state, if an overshoot made by the blades returning to the zero positions exceeds a predetermined limit, switches the first control state to the second control state, that when the second control state is designated, forcibly reverses the rotating direction of the motor so as to withdraw the blades, and that if an operator performs a manipulation to reset the collimator to the first control state, resets the collimator to the first control state based on tentative zero positions or the first control state based on the sense signal sent from the sensor according to whether the sensor has failed.

For solving the aforesaid problem, according to the third aspect of the present invention, there is provided a radiography system including an X-ray tube, a collimator that includes motor-driven blades and reshapes an X-ray beam irradiated from the X-ray tube to a subject of radiography, and a control apparatus that controls the collimator. The control apparatus includes: an encoder that encodes rotations made by the motor; a decoder that decodes a signal sent from the encoder; a sensor that senses whether the blades exist at zero positions; and a control means that when the collimator enters a homing phase in the first control state, positions the blades on the basis of a blade sense signal sent from the sensor, that if the sensor has not sensed the blades but the rotational velocity of a motor has decreased to fall below a predetermined speed, switches the first control state to the second control state, that when the collimator enters a working phase in the first control state, if an overshoot made by the blades returning to the zero positions exceeds a predetermined limit, switches the first control state to the second control state, that when the second control state is designated, forcibly reverses the rotating direction of the motor so as to withdraw the blades, and that if an operator performs a manipulation to reset the collimator to the first control state, resets the collimator to the first control state based on tentative zero positions or the first control state based on the sense signal sent from the sensor according to whether the sensor has failed.

Preferably, the rotational velocity is obtained as a measured value of a time required for the motor to make a unit rotation so that a signal inversely proportional to the velocity can be produced.

Preferably, the measured value is a value measured by counting the number of clock pulses so that an accurate measured value can be obtained.

Preferably, the pulse-repetition rate of clock pulses is expressed as follows:

$$f_{base} = R_{coff} \cdot V_0 \cdot N_{cyc}/60$$

where $R_{coff}$ denotes a resolution coefficient, $V_0$ denotes the number of rotations made by the motor with no load imposed on the motor, and $N_{cyc}$ denotes the number of encoder pulses per rotation of the motor.

Preferably, an indication signifying that the first control state has been switched to the second control state is displayed so that a present state can be known easily.

According to the aforesaid aspects of the present invention, when a collimator including motor-driven blades is controlled, an encoder is used encode rotations made by a motor, a decoder is used to decode a signal sent from the encoder, and a sensor is used to sense whether the blades exist at zero positions.

When the collimator enters a homing phase in the first control state, the blades are positioned based on a blade sense signal sent from the sensor. If the sensor has not sensed the blades but the rotational velocity of the motor has decreased to fall below a predetermined velocity, the first control state is switched to the second control state.

When the collimator enters a working phase in the first control state, if an overshoot made by the collimator returning to the zero positions exceeds a predetermined limit, the first control state is switched to the second control state. When the second control state is designated, the rotating direction of the motor is forcibly reversed in order to withdraw the blades. If an operator performs a manipulation to reset the collimator to the first control state, the collimator is reset to the first control state based on tentative zero positions or the first control state based on the sense signal sent from the sensor according to whether the sensor has failed. Consequently, a collimator control method and apparatus that do not cause the blades to get stuck and a radiography system including the collimator control apparatus can be realized.

Further objects and advantages of the present invention will be apparent from the following description of the preferred embodiments of the invention as illustrated in the accompanying drawings.

DETAILED DESCRIPTION OF THE INVENTION

Figure 1:
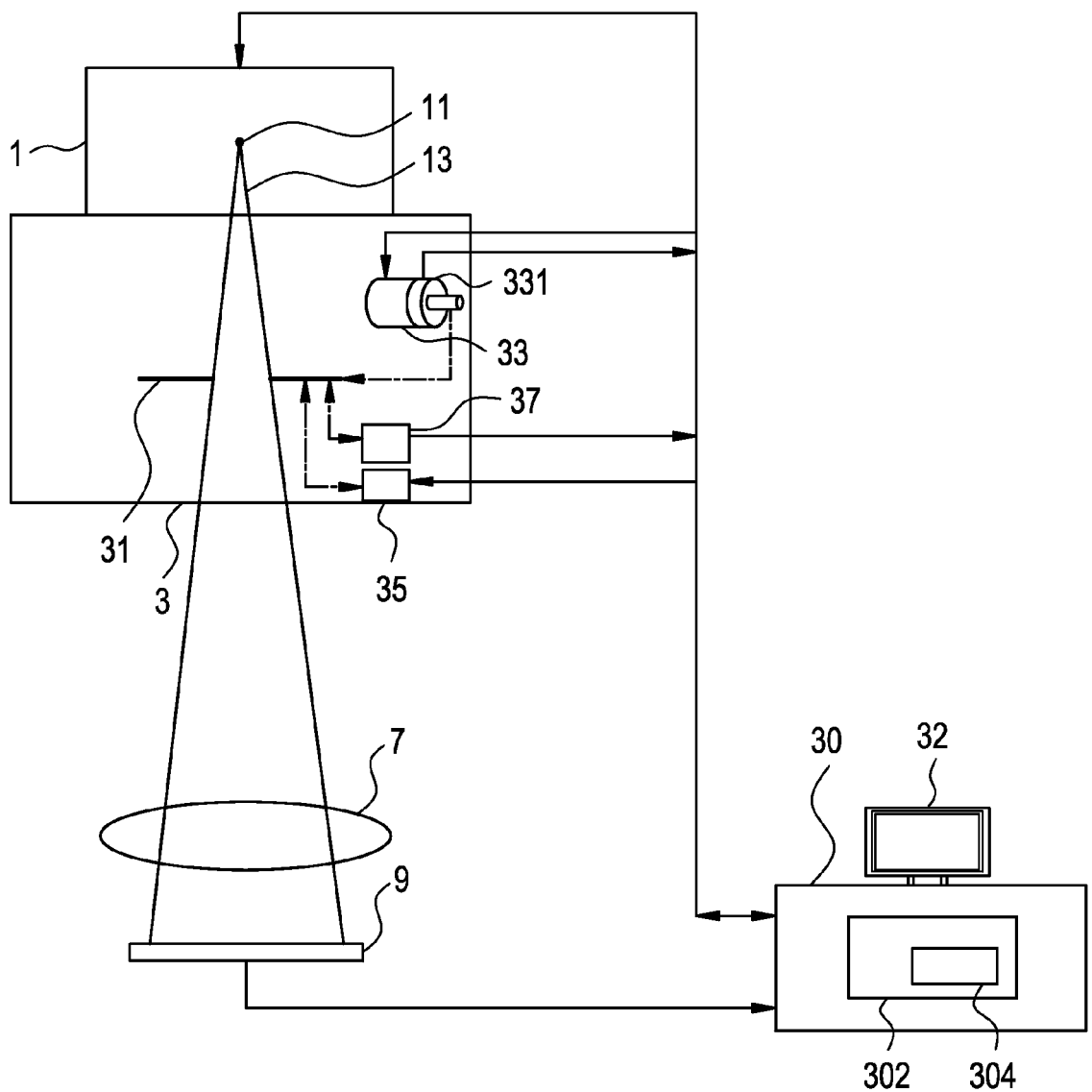
FIG. 1 shows the configuration of a radiography system that is an example of the best mode for implementing the present invention.

Referring to drawings, the best mode for implementing the present invention will be described below. Noted is that the present invention is not limited to the best mode for implementing the present invention. FIG. 1 illustratively shows a radiography system. The radiography system is an example of the best mode for implementing the present invention. The configuration of the radiography system presents examples of the best modes for implementing the present invention in a radiography system and in a collimator control apparatus alike. Actions to be performed in the radiography system present an example of the best mode for implementing the present invention in a collimator control method.

As shown in FIG. 1, a radiography system is such that: X-rays 13 radiated from a focal spot 11 in an X-ray tube 1 are irradiated to a subject of radiography 7 with an X-ray field limited by a pair of blades 31 included in a collimator 3; and a detector 9 detects transmitted X-rays. The X-ray tube 1 is an example of an X-ray tube included in the present invention.

The collimator 3 is an example of a collimator included in the present invention. The blades 31 are an example of blades included in the present invention.

The pair of blades 31 is driven by a motor 33 and has the spacing between them varied, whereby an X-ray field is adjusted. The motor 33 includes an encoder 331. The encoder 331 encodes rotations made by the motor 33. A braking mechanism 35 brakes the blades 31. The encoder 331 is an example of an encoder included in the present invention. The braking mechanism 35 is an example of a braking means included in the present invention.

The motor 33 is an example of a motor included in the present invention. The encoder 331 is an example of an encoder included in the present invention. The braking mechanism 35 is an example of a braking means included in the present invention.

A sensor 37 senses the reference position of the paired blades 31. Hereinafter, the reference position may be called a zero position. The sensor 37 is realized with, for example, an optical sensor. The sensor 37 is an example of a sensor included in the present invention.

A signal detected by the detector 9 is transferred to an operator console 30. The operator console 30 includes a computer 302. The computer 302 includes a memory 304.

The operator console 30 reconstructs fluoroscopic images of the subject of radiography 7 according to an input signal received from the detector 9, and displays the images on a display 32. The detector 9 may be made of a photosensitive material that emits light when bombarded by X-rays. In this case, the fluoroscopic images are made visible through development.

The operator console 30 controls the X-ray tube 1 and the collimator 3 according to input signals, which are received from the sensor 37 and encoder 331 respectively, while being manipulated by an operator. The operator console 30 uses a built-in decoder to decode the input signal received from the encoder.

As for the X-ray tube 1, the intensity of X-rays and the timing of irradiating X-rays are controlled. The collimator 3 has the movements of the blades 31 controlled via the motor 33. For control of the motor 33, the encoder 331 and a feedback signal sent from the sensor 37 are employed. The blades 31 are braked by the braking mechanism 35. The operator console 30 realizes a control apparatus together with the encoder 331 and sensor 37. The control apparatus is an example of a control apparatus included in the present invention.

The blades 31 support two moving phases. One of the phases is a homing phase, and the other is a working phase.

The homing phase is a phase in which the blades 31 are set to the zero position (homed). Homing is performed as one of preparations to be made before the radiography system is started. The working phase is a phase in which the blades 31 are driven in order to adjust an X-ray field while the radiography system is in operation.

Figure 2:
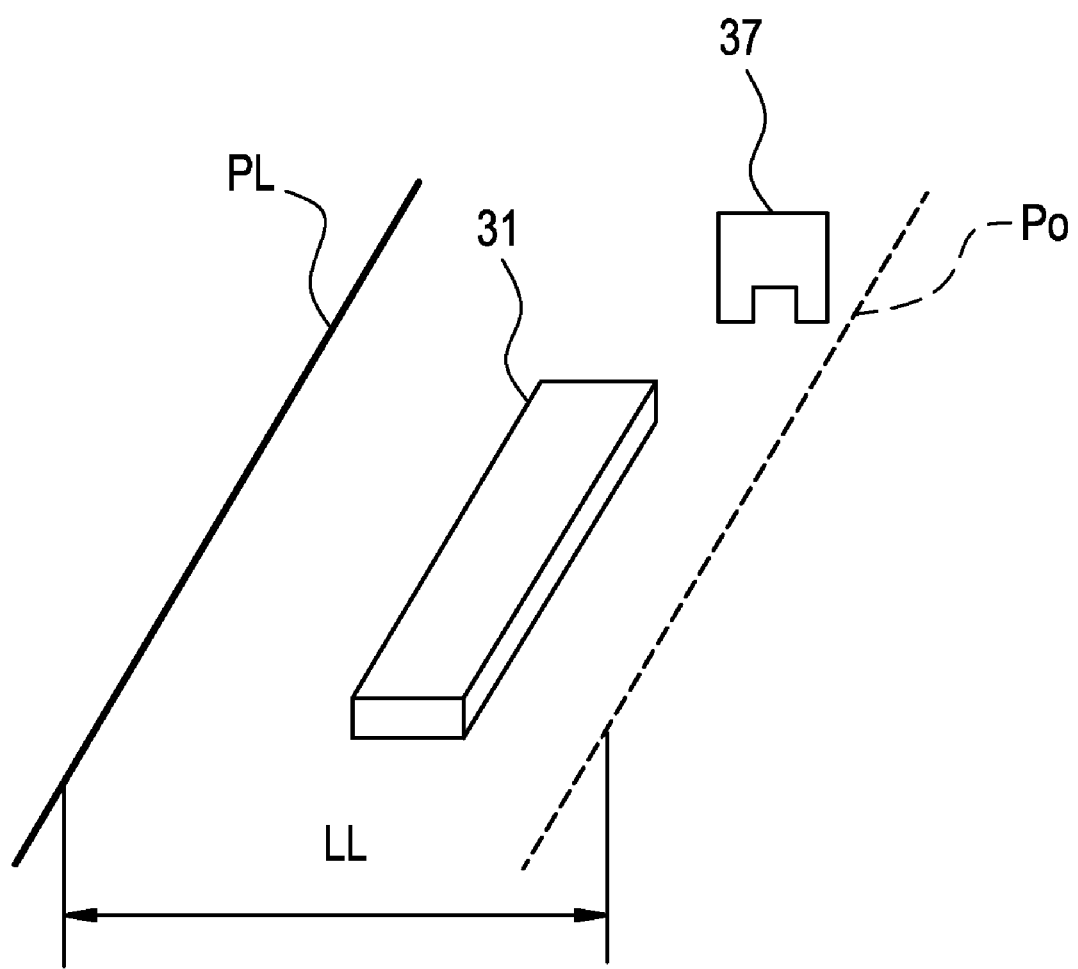
FIG. 2 shows the relationship between blades and a sensor established near a zero position.

The movements of the blades in the homing phase will be described below. FIG. 2 illustratively shows the relationship between the blades 31 and the sensor 37 established near the zero position. Herein, one of the paired blades is shown. The same applies to the other blade.

The sensor 37 senses whether the blades 31 are present at the zero position P0. Limit positions PL are set to positions separated from the zero position P0 by a distance LL in directions in which the blades recede from the zero position P0. A stopper that is not shown is disposed at each of the limit positions in order to hinder the blades 31 from receding farther.

Figure 3:
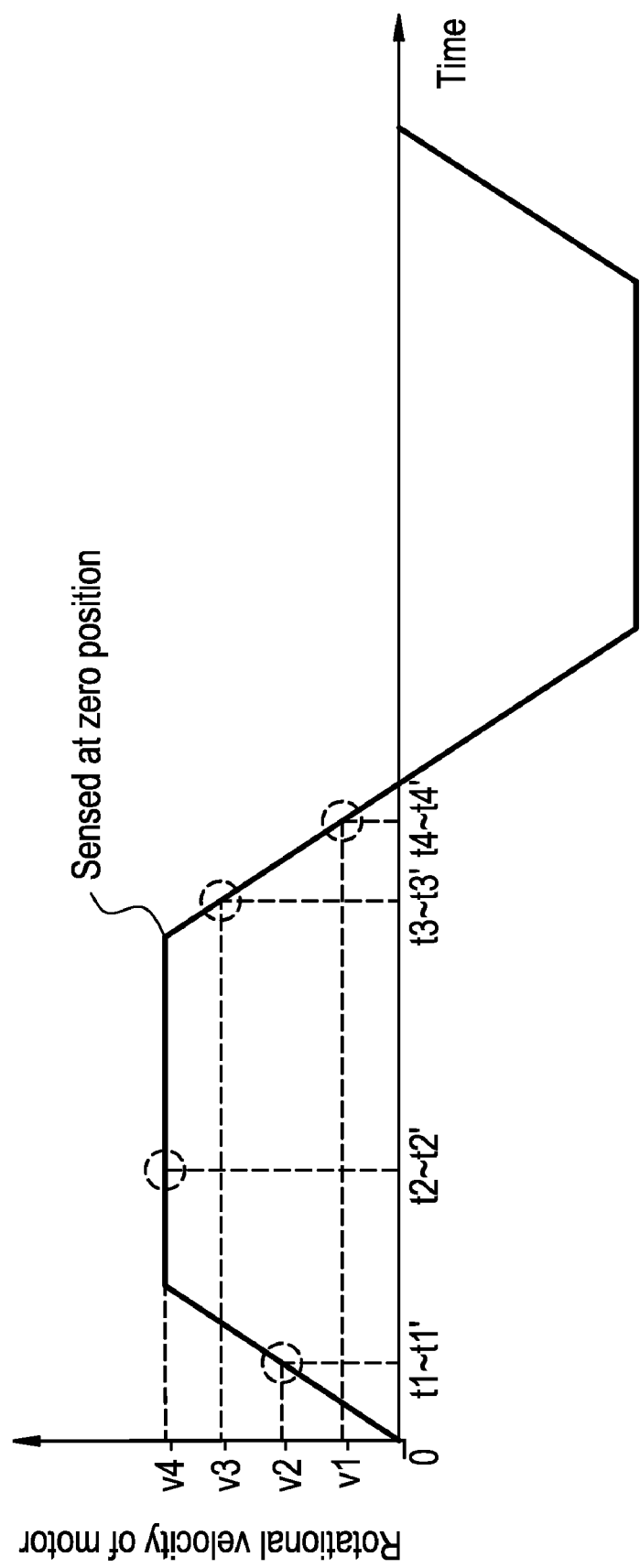
FIG. 3 shows a pattern of rotational velocities exhibited by a motor during homing.

Homing is achieved by moving the blades 31 toward the zero position P0. FIG. 3 shows a pattern of rotational velocities exhibited by the motor 33 during homing. When the motor 33 is rotated in a forward direction, the rotational velocity of the motor 33 gradually increases from zero and then becomes constant. Since the blades 31 are braked when they almost reach the zero position P, the rotational velocity of the motor 33 decreases to zero. The same applies to a case where the motor is rotated in a reverse direction.

The motor is rotated at a velocity V2 during a period from a time instant t1 to a time instant t1', and at a velocity V4 during a period from a time instant t2 to a time instant t2'. The motor is rotated at a velocity V3 during a period from a time instant t3 to a time instant t3', and at a velocity V1 during a period from a time instant t4 to a time instant t4'. The rotational velocities V1, V2, V3, and V4 get larger in that order.

Figure 4:
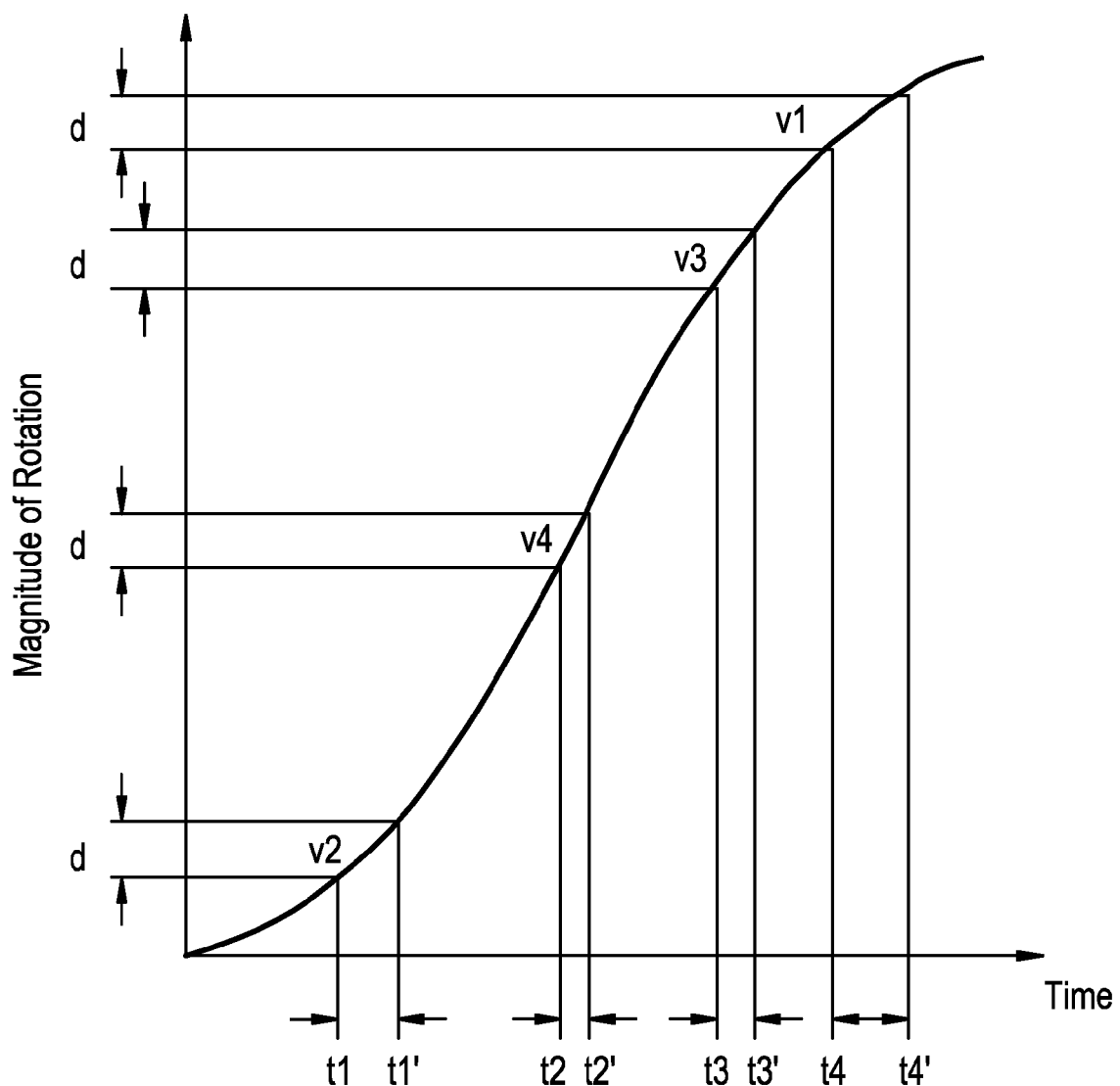
FIG. 4 shows a time-sequential change in a magnitude of rotation made by the motor 33.

FIG. 4 graphically shows a time-sequential change in a magnitude of rotation yielded by the motor 33 when the motor is rotated as mentioned above. The magnitude of rotation is proportional to the velocity, and a time required for rotation by a unit magnitude of rotation d is inversely proportional to the velocity.

Consequently, the length of the period between the time instants t1 and t1' is inversely proportional to the rotational velocity V2, the length of the period between the time instants t2 and t2' is inversely proportional to the rotational velocity V4, the length of the period between the time instants t3 and t3' is inversely proportional to the rotational velocity V3, and the length of the period between the time instants t4 and t4' is inversely proportional to the rotational velocity V1.

Figure 5:
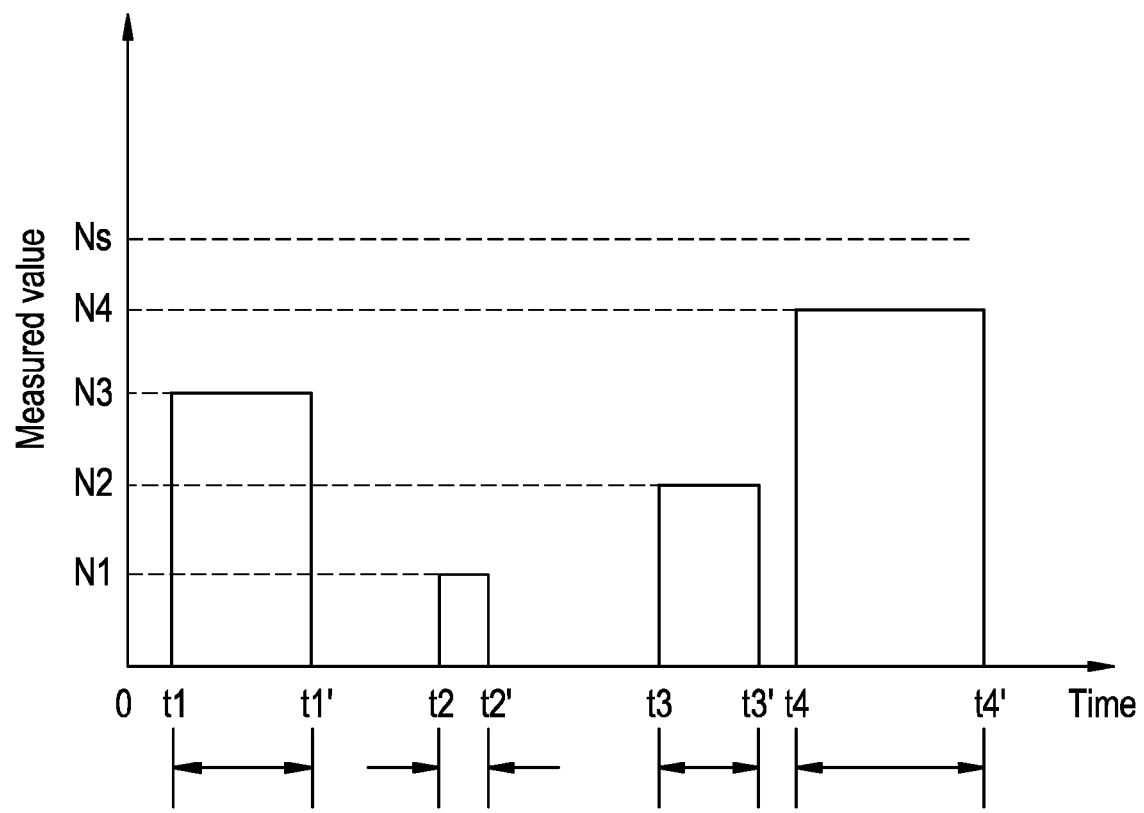
FIG. 5 graphically shows measured values in association with lengths of periods.

Each of the lengths of the periods is measured by counting the number of clock pulses, whereby measured values are plotted as in FIG. 5. Since the rotational velocity is obtained as a measured value of a time required for the motor to make a unit rotation, a signal inversely proportional to the velocity is produced.

N1 denotes a value measured during the period between the time instants t2 and t2', N2 denotes a value measured during the period between the time instants t3 and t3', N3 denotes a value measured during the period between the time instants t1 and t1', and N4 denotes a value measured during the period between the time instants t4 and t4'. The measured values N1, N2, N3, and N4 get larger in that order.

The pulse-repetition rate of clock pulses is expressed as follows:

$$f_{base} = R_{coff} \cdot V_0 \cdot N_{cyc}/60 \quad \text{[Formula 5]}$$

where $R_{coff}$ denotes a resolution coefficient, $V_0$ denotes the number of rotations made by the motor with no load imposed on the motor, and $N_{cyc}$ denotes the number of encoder pulses per rotation of the motor. The employment of the clock pulses provides a high-resolution measured value.

A set value Ns is determined in order to sense the fact that the blades 31 are stuck. The set value Ns is a value larger than the measured value N4.

When the set value Ns is converted to a rotational velocity, the rotational velocity is much lower than the velocity V1. The velocity V1 is the lowest velocity attained when the motor 33 is rotated normally. The set value Ns is determined to be equivalent to a velocity lower than the lowest velocity.

Figure 6:
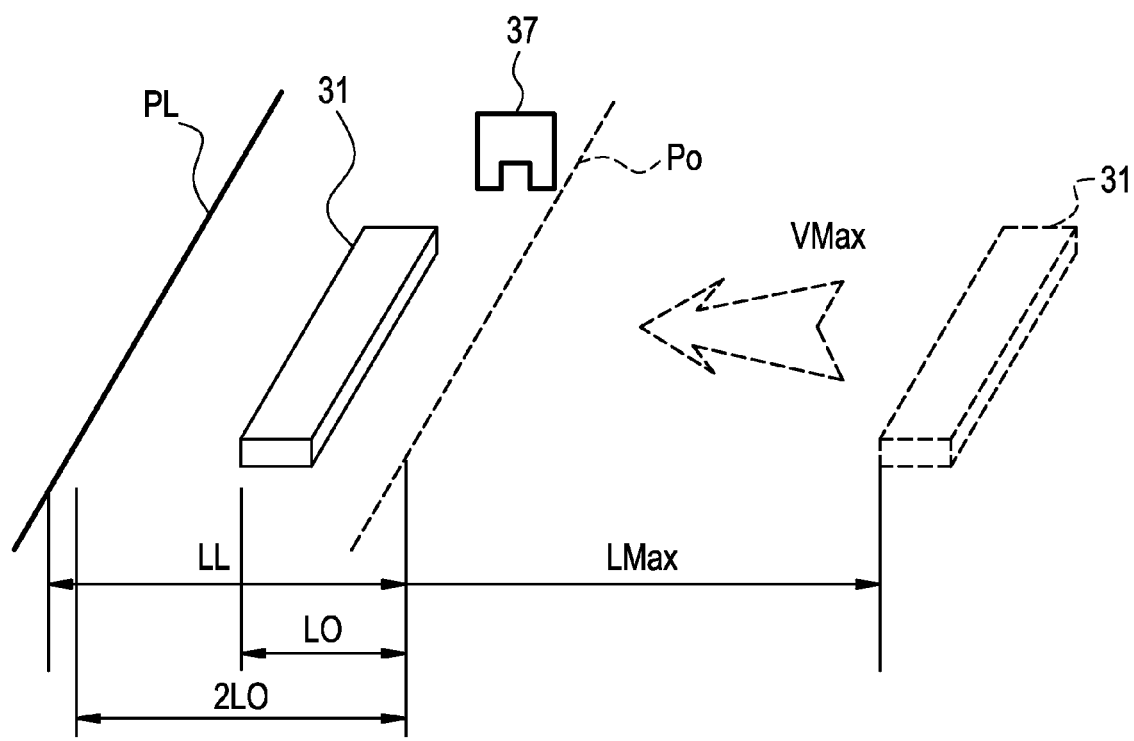
FIG. 6 shows a movement made by the blades in a working phase.

Movements made by the blades 31 in the working phase will be described below. In the working phase, a situation in which the blades 31 approach the zero position P0 as shown in FIG. 6 takes place.

At this time, the blades 31 are controlled to halt at the zero position P0. However, if the blades 31 are moved at a high velocity, the blades overshoot the zero position P0 due to inertia and then come to a halt.

In compliance with the property of the blades to be controlled, an upper limit of an overshoot is determined in order to detect an abnormal movement made by the blades 31. FIG. 6 shows an example of the determined upper limit of an overshoot. As shown in FIG. 6, the upper limit of an overshoot is determined as a distance LO from the zero position P0.

The upper limit LO is determined to be a bit larger than an overshoot caused when the blades 31 approach the zero position at the highest velocity VMax from respective positions separated by the longest distance LMax from the zero position. The overshoot is calculated or actually measured. The distance from the zero position P0 to the limit positions PL is determined to be larger than a value 2LO.

Figure 7:
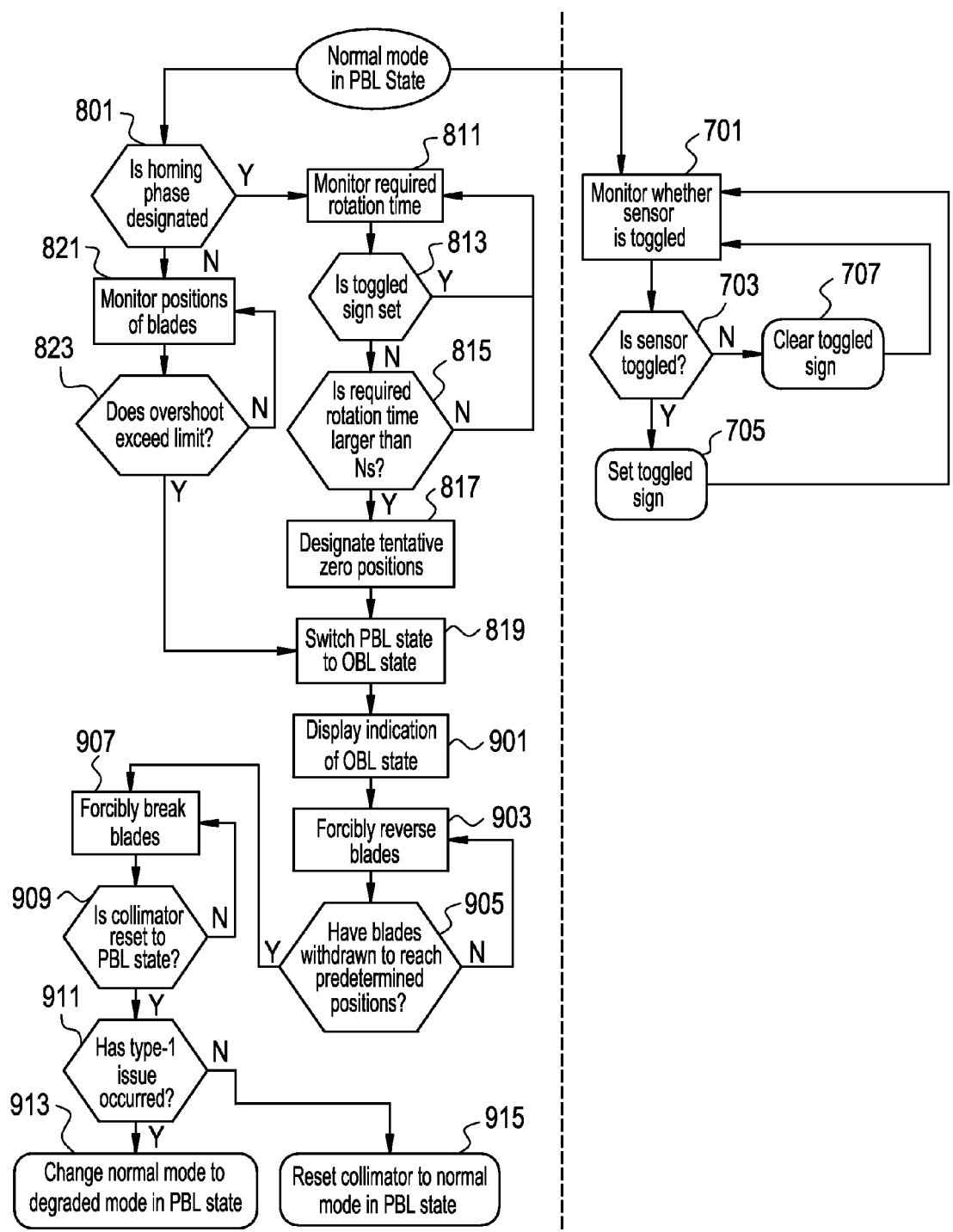
FIG. 7 is a flowchart describing actions to be performed in the radiography system that is an example of the best mode for implementing the present invention.

Actions to be performed in the radiography system will be described below. FIG. 7 is a flowchart describing a blade control procedure. The blade control procedure is followed by the computer 302. The computer 302 is an example of a control means included in the present invention.

Incidentally, firmware included in the collimator 3, such as, a field programmable gate array (FPGA) or a complex programmable logic device (CPLD) may be substituted for the computer 302.

When the collimator enters a normal mode in a positive beam limitation (PBL) state that is one of control states, control whose sequence is described in the right-hand flowchart of FIG. 7 is extended concurrently with control whose sequence is described in the left-hand flowchart thereof. The PBL state is a state in which control is extended based on a zero-position sense signal. The normal mode is a mode in which control is extended based on the sense signal sent from the sensor 37. The PBL state is an example of the first control state supported by the present invention.

According to the right-hand flowchart, at step 701, the sense signal sent from the sensor is monitored. At step 703, the sense signal is checked to see if it indicates a toggled state. When it says that the sense signal indicates a toggled state, it means that the sensor 37 has sensed the blades 31.

If the sense signal is recognized to indicate a toggled state, a Toggled sign is set at step 705. Control is then returned to step 701. If the sense signal is not recognized to indicate a toggled state, the Toggled sign is cleared at step 707 and control is returned to step 701. This action is performed in the normal mode in the PBL state all the time.

According to the left-hand flowchart, at step 801, a determination is made of whether the collimator has entered a homing phase. If the collimator is recognized to have entered the homing phase, a required rotation time is monitored.

What is referred to as the required rotation time is the time required for the motor 33 to make a unit rotation d as shown in FIG. 4. The time is always measured by counting the number of clock pulses.

At step 813, the Toggled sign is checked to see if it is set. If the Toggled sign is recognized to have been set, control is returned to step 811 and the required rotation time is monitored. While the Toggled sign is held set, the actions of steps 811 to 813 are repeated.

If the Toggled sign is not recognized to have been set, the required rotation time is checked at step 815 to see if it is larger than Ns. If the required rotation time is not larger than Ns, control is returned to step 811 and the required rotation time is monitored. As long as the Toggled sign is not set and the required rotation time is not larger than Ns, the actions of step 811 to 815 are repeated.

When the sensor 37 fails, even if the blades 31 have reached the zero positions P0, the fact is not sensed. The braking mechanism 35 is not actuated accordingly. The blades 31 overshoot the zero positions P0 and collide with the stoppers at the limit positions PL.

When the blades 31 collide with the stoppers, the motor 33 that drives the blades is overloaded. The number of rotations made by the motor decreases, and the required rotation time gets larger than Ns. In this case, the required rotation time is recognized to be larger than Ns at step 815.

Based on the recognition made at step 815, tentative zero positions are determined at step 817. The tentative zero positions are inferred from the known relationship of correspondence between the zero positions and a decoded value of a signal sent from the encoder 331.

At step 819, the PBL state is switched to an override beam limitation (OBL) state. What is referred to as the OBL state is a control state in which control is extended irrespective of a zero-position sense signal. The OBL state is an example of the second control state supported by the present invention.

On the other hand, when the collimator enters the working phase, the homing phase is not recognized at step 801. In this case, the positions of the blades are monitored at step 821. The positions of the blades are monitored based on a decoded value of a signal sent from the encoder 331.

At step 823, an overshoot is checked to see if it exceeds a limit. If the overshoot does not exceed the limit, control is returned to step 821 and the positions of the blades are monitored. As long as the overshoot does not exceed the limit, the actions of steps 821 to 823 are repeated.

The blades 31 may overshoot by a length exceeding the upper limit LO because of an abnormality in a control system or an operator's improper manipulation. In this case, the overshoot is recognized to have exceeded the limit at step 823. At step 819, the PBL state is switched to the OBL state.

As mentioned above, if the sensor 37 fails or the control system becomes abnormal, the PBL state is automatically switched to the OBL state. In the OBL state, an indication of the OBL state is displayed at step 901. This helps an operator readily recognize the fact that the control states have been switched. The indication of the OBL state is displayed on, for example, the display 32. The display 32 is an example of a display means included in the present invention. Incidentally, the indicator of the OBL state is not limited to the display 32 but may be an indicator lamp, a buzzer, or sounds.

At step 903, the blades are forcibly reversed. The forcible reversal of the blades is achieved by forcibly reversing the rotating direction of the motor 33. Consequently, the blades 31 are withdrawn from the limit positions PL or positions to which the blades have reached due to overshooting.

At step 905, the blades are checked to see if they have withdrawn to predetermined positions. The reversal of the blades of step 903 is continued until the blades have withdrawn to reach the predetermined positions.

When the blades have withdrawn to reach the predetermined positions, the blades are braked at step 907. The predetermined positions which the blades have withdrawn to reach are determined to correspond to the zero positions P0. Consequently, the blades 31 stand still at the zero positions P0.

As mentioned above, in the homing phase, the PBL state is switched to the OBL state on condition that the Toggled sign is not set and the required rotation time is larger than Ns. The blades are then forcibly reversed. The event that the blades 31 get stuck because of the failure of the sensor 37 can be avoided.

In the working phase, the PBL state is switched to the OBL state on condition that an overshoot exceeds a limit. The blades are then forcibly reversed. Consequently, the blades 31 are prevented from getting stuck.

Thereafter, at step 909, a determination is made of whether the collimator is reset to the PBL state. An operator determines whether the collimator should be reset to the PBL state. The operator performs a predetermined manipulation according to his/her determination.

When a manipulation is performed to reset the collimator to the PBL state, a determination is made of whether a type-1 issue has occurred at step 911.

What is referred to as the type-1 issue is an event that the PBL state should be switched to the OBL state because of the failure of the sensor 37. Consequently, when the PBL state is switched to the OBL state in the homing phase, the type-1 issue has occurred. When the PBL state is switched to the OBL state in the working phase, the type-1 issue has not occurred.

When the type-1 issue has occurred, the normal mode in the PBL state is changed to a degraded mode therein at step 913. The degraded mode in the PBL state is a mode in which the PBL state is controlled based on tentative zero positions. Since control is extended based on the tentative zero positions, although the sensor 37 has failed, the blades 31 can be homed. However, since the homing is performed based on the tentative zero positions, the precision in the homing is not guaranteed. Nevertheless, this is better than an event that homing is impossible to do.

When the type-1 issue has not occurred, the collimator is reset to the normal mode in the PBL state at step 915. The normal mode in the PBL state is a mode in which the PBL state is controlled based on the sense signal sent from the sensor 37. In this mode, since control is extended based on the sense signal sent from the sensor 37, the blades 31 are homed highly precisely.

Many widely different embodiments of the invention may be configured without departing from the spirit and the scope of the present invention. It should be understood that the present invention is not limited to the specific embodiments described in the specification, except as defined in the appended claims.

The invention claimed is:

1. A collimator control method for controlling a collimator that
includes motor-driven blades, comprising the steps of:
using an encoder to encode rotations made by a motor;
using a decoder to decode a signal sent from the encoder;
using a sensor to sense whether the blades exist at zero positions;
positioning, when the collimator enters a homing phase in a first control state, the blades on the basis of a blade sense signal sent from the sensor, and if the sensor has not sensed the blades but the rotational velocity of the motor has decreased to fall below a predetermined velocity, switching the first control state to the second control state;
switching the first control state to the second control state when the collimator enters a working phase in the first control state and when an overshoot made by the blades returning to the zero positions exceeds a predetermined limit;
forcibly reversing, when the second control state is designated, the rotating direction of the motor so as to withdraw the blades, and if an operator performs a manipulation to reset the collimator to the first control state, resetting the collimator to the first control state based on tentative zero positions or the first control state based on the sense signal sent from the sensor according to whether the sensor has failed.

2. The collimator control method according to claim 1, wherein the rotational velocity is obtained as a measured value of a time required for the motor to make a unit rotation.

3. The collimator control method according to claim 2, wherein the measured value is a value measured by counting the number of clock pulses.

4. The collimator control method according to claim 3, wherein the pulse-repetition rate of clock pulses is expressed as follows:

$$f_{base} = R_{coff} \cdot V_0 \cdot N_{cyc}/60$$

where Rcoff denotes a resolution coefficient, V0 denotes the number of rotations made by the motor with no load imposed on the motor, and Ncyc denotes the number of encoder pulses per rotation of the motor.

5. The collimator control method according to claim 1, wherein an indication signifying that the first control state has been switched to the second control state is displayed.

6. A collimator control apparatus for controlling a collimator that includes motor-driven blades, comprising:
an encoder that encodes rotations made by a motor;
a decoder that decodes a signal sent from the encoder;
a sensor that senses whether the blades exist at zero positions; and
a control device that when the collimator enters a homing phase in a first control state, positions the blades on the basis of a blade sense signal sent from the sensor, that if the sensor has not sensed the blades but the rotational velocity of the motor has decreased to fall below a predetermined velocity, switches the first control state to the second control state, that when the collimator enters a working phase in the first control state, if an overshoot made by the blades returning to the zero positions exceeds a predetermined limit, switches the first control state to the second control state, that when the second control state is designated, forcibly reverses the rotating direction of the motor so as to withdraw the blades, and that if an operator performs a manipulation to reset the collimator to the first control state, resets the collimator to the first control state based on tentative zero positions or the first control state based on the sense signal sent from the sensor according to whether the sensor has failed.

7. The collimator control apparatus according to claim 6, wherein the control device obtains the rotational velocity as a measured value of a time required for the motor to make a unit rotation.

8. The collimator control apparatus according to claim 7, wherein the measured value is a value measured by counting the number of clock pulses.

9. The collimator control apparatus according to claim 8, wherein the pulse-repetition rate of clock pulses is expressed as follows:

$$f_{base} = R_{coff} \cdot V_0 \cdot N_{cyc}/60$$

where Rcoff denotes a resolution coefficient, V0 denotes the number of rotations made by the motor with no load imposed on the motor, and Ncyc denotes the number of encoder pulses per rotation of the motor.

10. The collimator control apparatus according to claim 6, further comprising a display device on which an indication signifying that the first control state has been switched to the second control state is displayed.

11. A radiography system including an X-ray tube, a collimator that includes motor-driven blades and reshapes an X-ray beam irradiated from the X-ray tube to a subject of radiography, and a control apparatus that controls the collimator, wherein the control apparatus comprises:
an encoder that encodes rotations made by a motor;
a decoder that decodes a signal sent from the encoder;
a sensor that senses whether the blades exists at zero positions; and
a control device that when the collimator enters a homing phase in a first control state, positions the blades on the basis of a blade sense signal sent from the sensor, that if the sensor has not sensed the blades but the rotational velocity of the motor has decreased to fall below a predetermined velocity, switches the first control state to the second control state, that when the collimator enters a working phase in the first control state, if an overshoot made by the blades returning to the zero positions exceeds a predetermined limit, switches the first control state to the second control state, that when the second control state is designated, forcibly reverses the rotating direction of the motor so as to withdraw the blades, and that if an operator performs a manipulation to reset the collimator to the first control state, resets the collimator to the first control state based on tentative zero positions or the first control sate based on the sense signal sent from the sensor according to whether the sensor has failed.

12. The radiography system according to claim 11, wherein the control device obtains the rotational velocity as a measured value of a time required for the motor to make a unit rotation.

13. The radiography system according to claim 12, wherein the measured value is a value measured by counting the number of clock pulses.

14. The radiography system according to claim 13, wherein the pulse-repetition rate of clock pulses is expressed as follows:

$$f_{base} = R_{coff} \cdot V_0 \cdot N_{cyc}/60$$

where Rcoff denotes a resolution coefficient, $V_0$ denotes the number of rotations made by the motor with no load imposed on the motor, and Ncyc denotes the number of encoder pulses per rotation of the motor.

15. The radiography system according to claim 11, further comprising a display device on which an indication signifying that the first control state has been switched to the second control state is displayed.

* * * * *